US 7,780,731 B2

(12) United States Patent  (10) Patent No.: US 7,780,731 B2
Marnay et al.  (45) Date of Patent: Aug. 24, 2010

(54) INTERVERTEBRAL IMPLANT

(75) Inventors: Theirry Marnay, Castelnau le Lez (FR);
John Paul Furda, Hamilton, NJ (US);
David Gerber, West Chester, PA (US)

(73) Assignee: Spine Solutions, Inc., West Chester, PA (US)

( * ) Notice: Subject to any disclaimer, the term of this patent is extended or adjusted under 35 U.S.C. 154(b) by 1137 days.

(21) Appl. No.: 10/996,797

(22) Filed: Nov. 26, 2004

(65) Prior Publication Data

US 2006/0116769 A1 Jun. 1, 2006

(51) Int. Cl.
*A61F 2/44* (2006.01)
(52) U.S. Cl. .................................................. 623/17.11
(58) Field of Classification Search .... 623/17.11–17.16
See application file for complete search history.

(56) References Cited

U.S. PATENT DOCUMENTS

| | | | |
|---|---|---|---|
| 4,759,766 A | 7/1988 | Buettner-Janz et al. | |
| 4,772,287 A | 9/1988 | Ray et al. | |
| 5,314,477 A | 5/1994 | Marnay | |
| 5,397,364 A | 3/1995 | Kozak et al. | |
| 5,401,269 A * | 3/1995 | Buttner-Janz et al. | 623/17.15 |
| 5,507,816 A | 4/1996 | Bullivant | |
| 6,315,797 B1 | 11/2001 | Middleton | |
| 6,368,350 B1 | 4/2002 | Erickson et al. | |
| 6,428,544 B1 * | 8/2002 | Ralph et al. | 606/99 |
| 6,533,817 B1 * | 3/2003 | Norton et al. | 623/17.16 |
| 6,607,558 B2 | 8/2003 | Kuras | |
| 6,626,943 B2 | 9/2003 | Eberlein et al. | |
| 6,645,248 B2 | 11/2003 | Casutt | |
| 6,656,224 B2 | 12/2003 | Middleton | |
| 6,676,703 B2 | 1/2004 | Biscup | |
| 6,682,562 B2 | 1/2004 | Viart et al. | |
| 7,503,934 B2 | 3/2009 | Eisermann et al. | |
| 2002/0128715 A1 | 9/2002 | Bryan et al. | |
| 2002/0156528 A1 | 10/2002 | Gau | |
| 2003/0135277 A1 | 7/2003 | Bryan et al. | |
| 2003/0135278 A1 | 7/2003 | Eckman | |
| 2003/0144736 A1 | 7/2003 | Sennett | |
| 2003/0176922 A1 | 9/2003 | Lawson et al. | |
| 2003/0195631 A1 | 10/2003 | Ferree | |
| 2003/0199984 A1 | 10/2003 | Trieu | |
| 2004/0002762 A1 | 1/2004 | Hawkins | |
| 2004/0010316 A1 | 1/2004 | William et al. | |
| 2004/0024462 A1 | 2/2004 | Ferree et al. | |

(Continued)

FOREIGN PATENT DOCUMENTS

EP   0 304 305   2/1989

(Continued)

*Primary Examiner*—David Isabella
*Assistant Examiner*—Ann Schillinger
(74) *Attorney, Agent, or Firm*—Woodcock Washburn LLP

(57) ABSTRACT

An intervertebral implant device includes an upper part, a lower part and a core element. The upper part includes an upper surface for engaging a vertebrae and a lower surface which includes a convex portion. The lower part includes a lower surface for engaging a vertebrae and an upper surface having a convex portion. The core element has an upper concave portion to operatively engage with the convex portion on the upper part and a lower concave portion to operatively engage with the convex portion of the lower part. Limited universal movement and translational movement is provided between the upper part and lower part.

32 Claims, 18 Drawing Sheets

U.S. PATENT DOCUMENTS

| | | |
|---|---|---|
| 2004/0093082 A1 * | 5/2004 | Ferree .................... 623/17.11 |
| 2004/0127992 A1 | 7/2004 | Serhan et al. |
| 2004/0133278 A1 | 7/2004 | Marino et al. |
| 2004/0133281 A1 | 7/2004 | Khandkar et al. |
| 2004/0138750 A1 | 7/2004 | Mitchell |
| 2004/0138753 A1 | 7/2004 | Ferree |
| 2005/0043802 A1 | 2/2005 | Eisermann et al. |

FOREIGN PATENT DOCUMENTS

| | | |
|---|---|---|
| WO | WO-03/084449 | 10/2003 |
| WO | WO/2005/053580 A1 | 6/2005 |

* cited by examiner

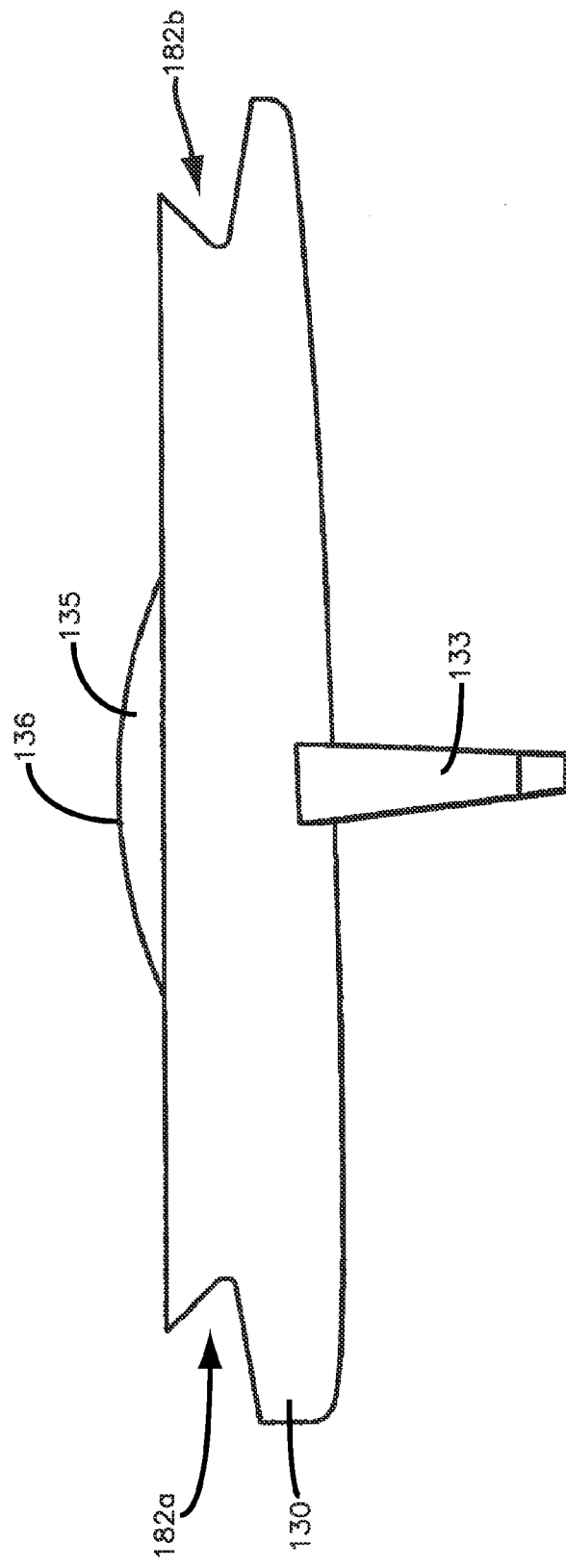

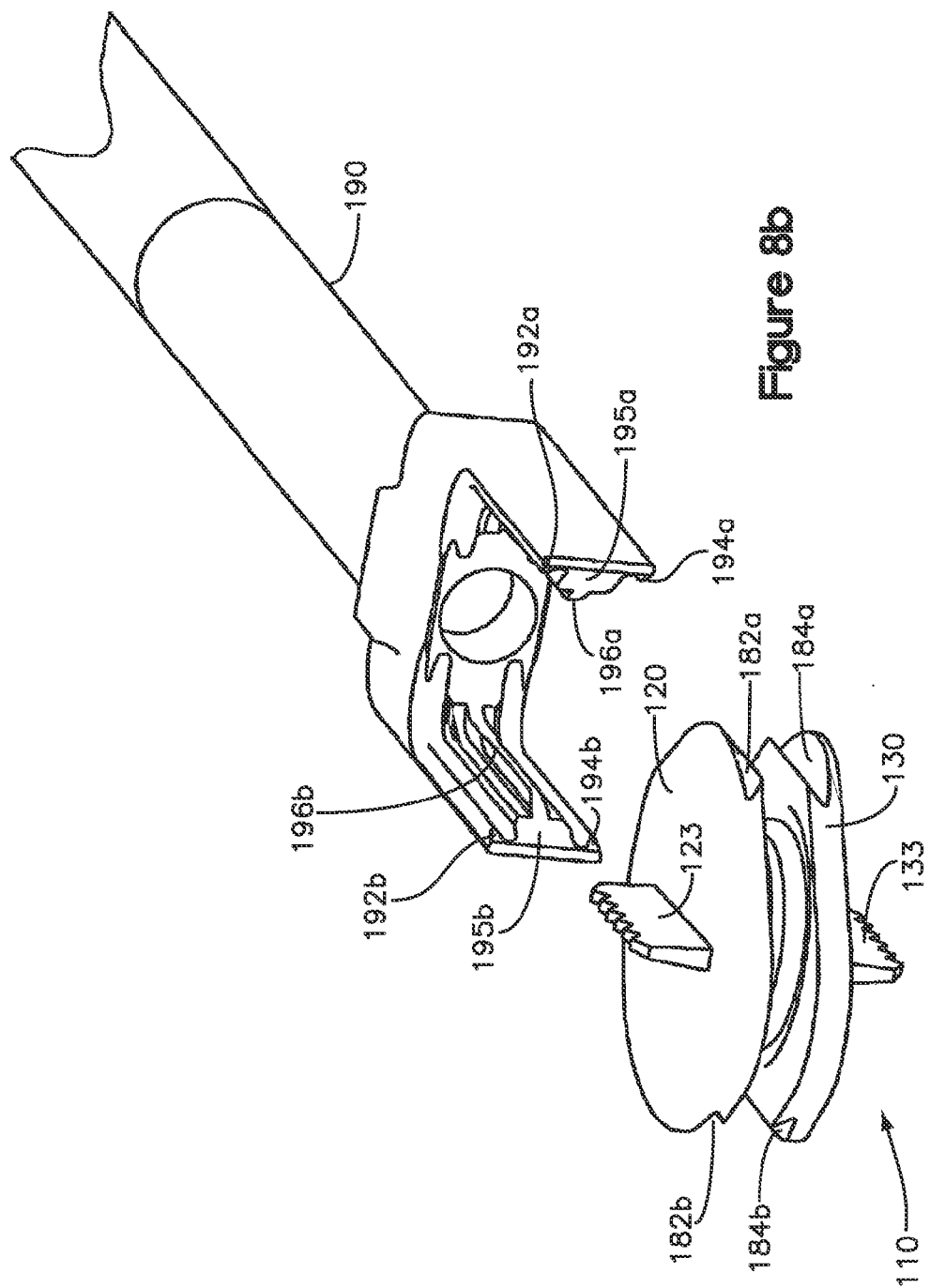

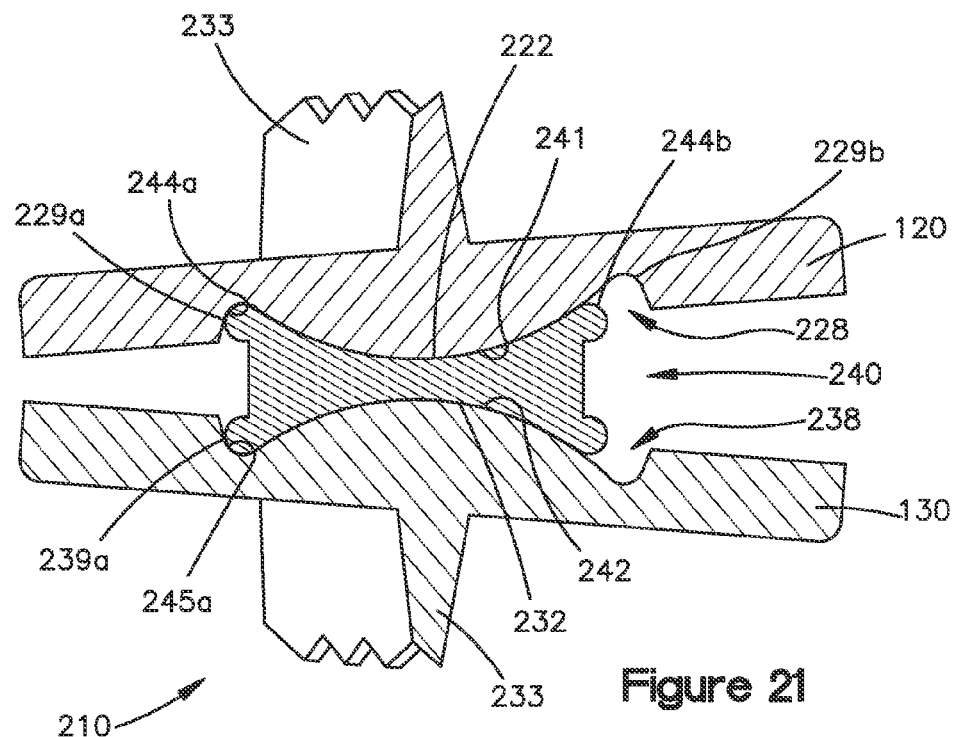
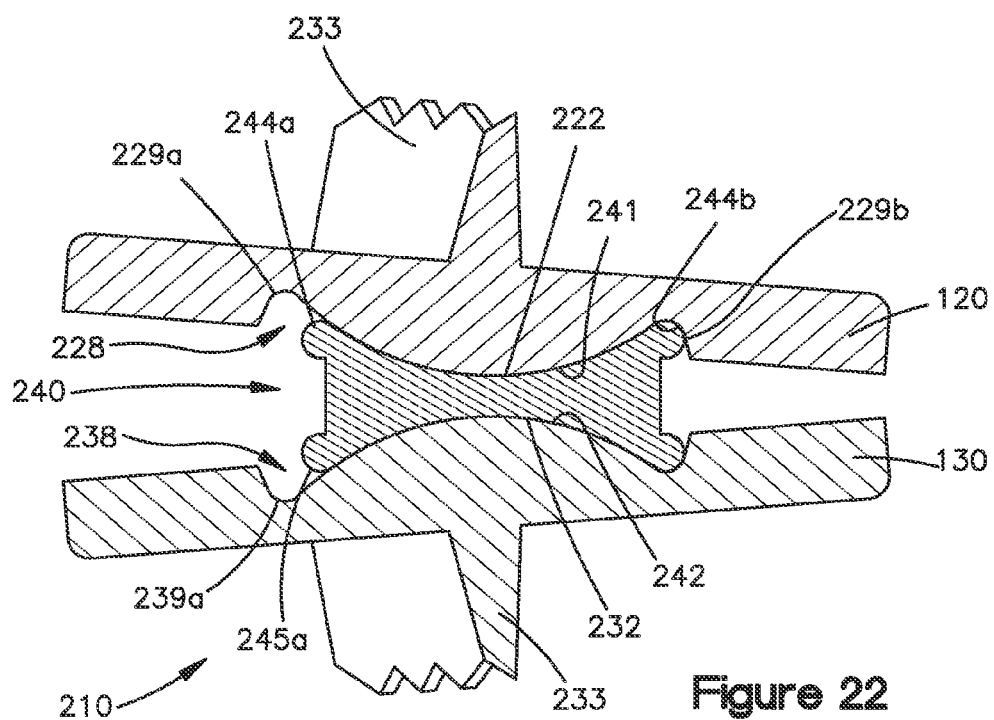

INTERVERTEBRAL IMPLANT

FIELD OF THE INVENTION

The present invention relates to an intervertebral implant, and more specifically, the present invention relates to an intervertebral implant which permits a wider degree of motion of the adjacent vertebrae.

BACKGROUND OF THE INVENTION

Prior intervertebral implants are disclosed by U.S. Pat. No. 5,314,477 and U.S. Patent Publication Application No. 2004/0215198. These references disclose implants which replace a disc removed from the intervertebral space using a total disc replacement procedure. These and other devices have been used in the field of disc replacement which involves the insertion of an artificial intervertebral disc implant into the intervertebral space between adjacent vertebrae, and which allows limited universal movement of the adjacent vertebrae with respect to each other.

Recently, several non-fusion techniques have emerged which treat different stages of degenerative disc disease other than total disc replacement. One of these technologies includes nucleus replacement devices which have been developed to treat early stages of degenerative disc disease. The goal of these technologies is to replace only the nucleus pulposus of the intervertebral disc and to leave the annulus and the ligaments as intact as possible.

Although these prior nucleus replacement intervertebral devices provide limited universal movement, there is a need in the art for new and improved intervertebral devices which provide enhanced universal movement of the adjacent vertebrae with respect to each other.

BRIEF SUMMARY OF THE INVENTION

The present invention relates to a new and improved intervertebral implant device which provides enhanced universal movement of the adjacent vertebrae with respect to each other. In one form, the present implant comprises three components, namely two end plates, i.e., an upper part and a lower part, each having a convex articulating surface, and a bi-concave core element disposed between the upper part and the lower part. The device can be inserted into the intervertebral space as a one-piece assembly or as individual components. Insertion is preferably through a lateral or anterolateral approach, while preserving the anterior and posterior longitudinal ligaments. Alternatively, the device can be inserted through an anterior approach. The present implant device replicates the moving nucleus within the intervertebral disc, while also preserving the stability of the segments, i.e., the two end plates and the core element, due to the preservation of anterior and posterior longitudinal ligaments when inserted using a lateral or anterolateral approach.

In one advantageous form, in addition to allowing universal motion in all directions, the present implant provides for horizontal translation of adjacent upper and lower vertebrae.

The present invention, in one form thereof, comprises an intervertebral implant device having an upper part with an upper surface for engaging a vertebrae and a lower surface which includes a convex portion. A lower part includes a lower surface for engaging a vertebrae and an upper surface having a convex portion. A core element has an upper concave portion operatively engaged with the convex portion of the upper part and a lower concave portion operatively engaged with the convex portion of the lower part. At least one of the upper or lower parts have a groove surrounding its convex portion.

The present invention, in another form thereof, comprises an intervertebral implant device having an upper part and a lower part and a core element therebetween. The upper part has an upper surface for engaging a vertebrae and a lower surface which includes a convex portion. The bottom part has a lower surface for engaging a vertebrae and an upper surface having a convex portion. The core element has an upper concave portion to operatively engage with the convex portion of the upper part and a lower concave portion to operatively engage with the convex portion of the lower part. The upper part and the lower part are laterally translatable relative to each other by surfaces of their respective convex portions sliding along surfaces of the concave portions of the core element.

In one advantageous form, movement of the upper part relative to the lower part is limited by the core element abutting upper part wall surfaces and lower part wall surfaces of grooves formed in the lower surface of the upper part and the upper surface of the lower part, respectively.

The present invention, in another form thereof, comprises an intervertebral implant device having an upper part having an upper surface for engaging a vertebrae and an upper inlay element dimensioned to be disposed in a recess formed therein. The upper inlay element has a lower surface which includes a convex surface facing opposite the upper part recess. The lower part has a lower surface for engaging a vertebrae and a lower inlay element is dimensioned to be disposed in a recess formed therein. The lower inlay element has an upper surface having a convex surface facing opposite the lower part recess. A core element has an upper concave portion which is operatively engaged with the convex surface of the upper part inlay element and a lower concave portion which is operatively engaged with the convex surface of the lower inlay element. The upper part and lower part are translatable relative to each other by surfaces of their respective convex surfaces sliding along surfaces of the concave portions of the core element.

In one advantageous form, movement of the upper part relative to the lower part is limited by the core element abutting upper part wall surfaces and lower part wall surfaces of grooves formed in the lower surface of the upper part and the upper surface of the lower part, respectively.

Objects of the present invention will be apparent from the detailed description to follow, together with the accompanying drawings.

BRIEF DESCRIPTION OF THE DRAWINGS

Preferred embodiments of the invention will now be described by way of example with reference to the accompanying drawings, wherein:

FIG. 8a is an elevation view of the lower plate of the device of FIG. 4 taken in the plane of line 8-8.

FIG. 8b is a perspective view of the device of FIG. 4 along with an insertion tool in accordance with the present invention.

FIG. 21 is a cross sectional view of the implant device of FIG. 16 taken in the plane of line 17-17 of FIG. 16, shown in a left lateral bend position.

FIG. 22 is a cross sectional view of the implant device of FIG. 16 taken in the plane of line 17-17 of FIG. 16, shown in a right lateral bend position.

DETAILED DESCRIPTION OF THE PREFERRED EMBODIMENTS

Figure 1:
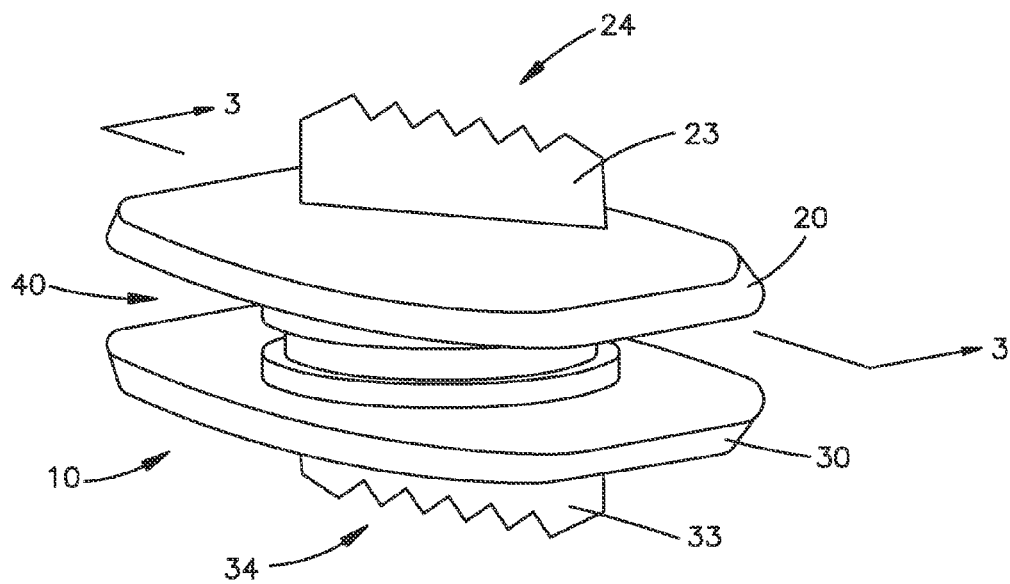
FIG. 1 is a perspective view of an intervertebral implant device in accordance with the present invention.

Referring now to the drawings, like elements are represented by like numerals throughout the several views.

Figure 2:
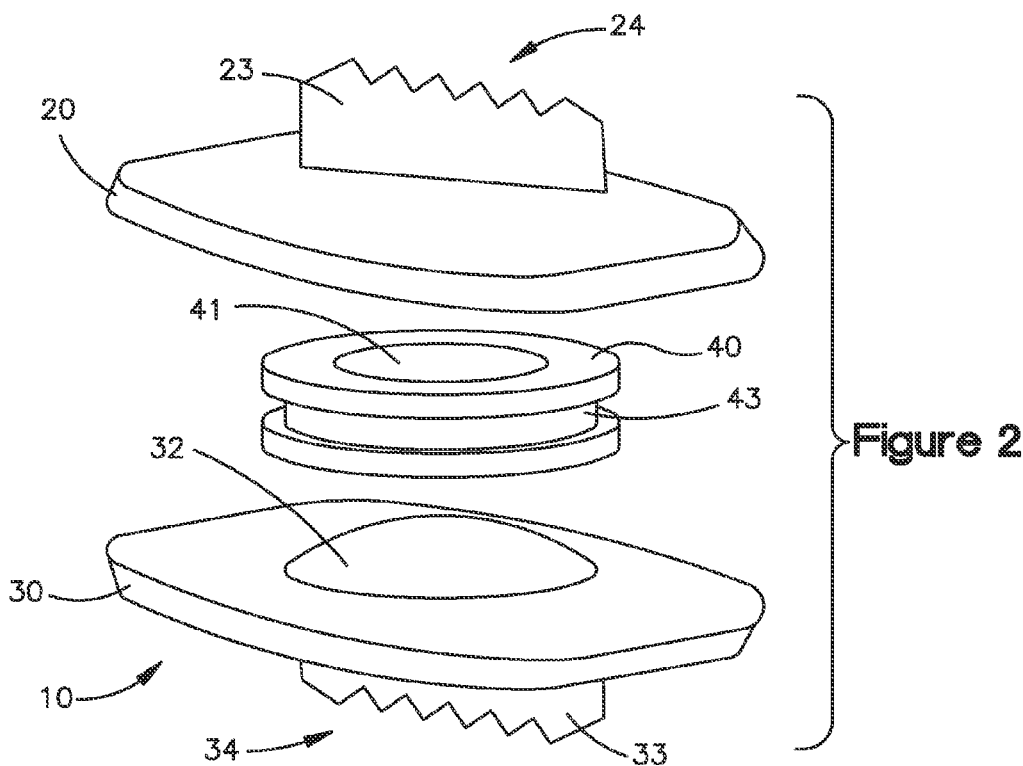
FIG. 2 is an exploded view of the implant device of FIG. 1.
Figure 3:
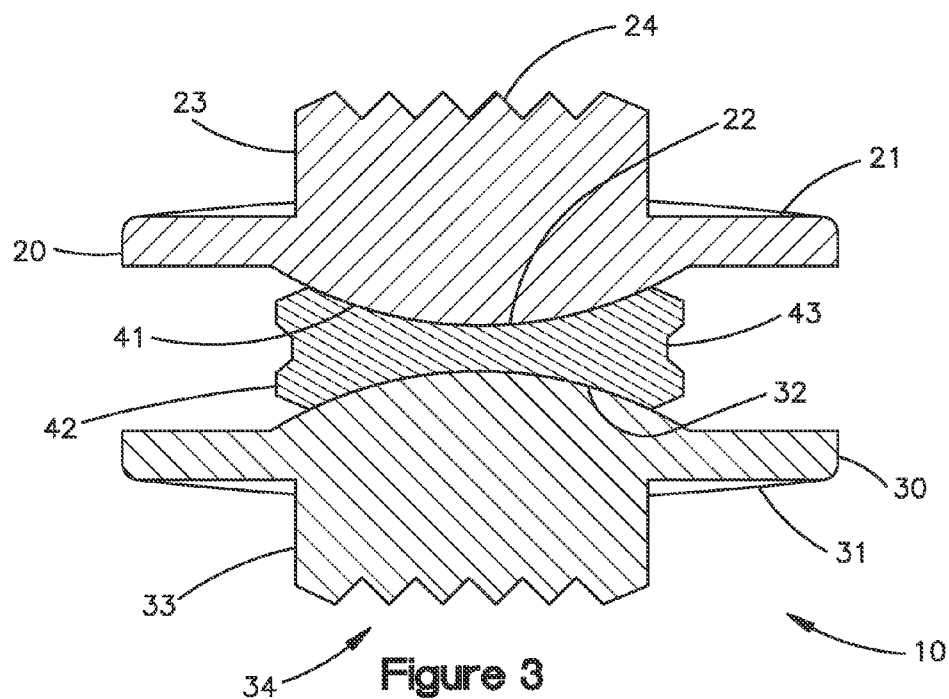
FIG. 3 is a cross sectional view of the implant device of FIG. 1 taken in the plane of line 3-3 of FIG. 1.
Figure 4:
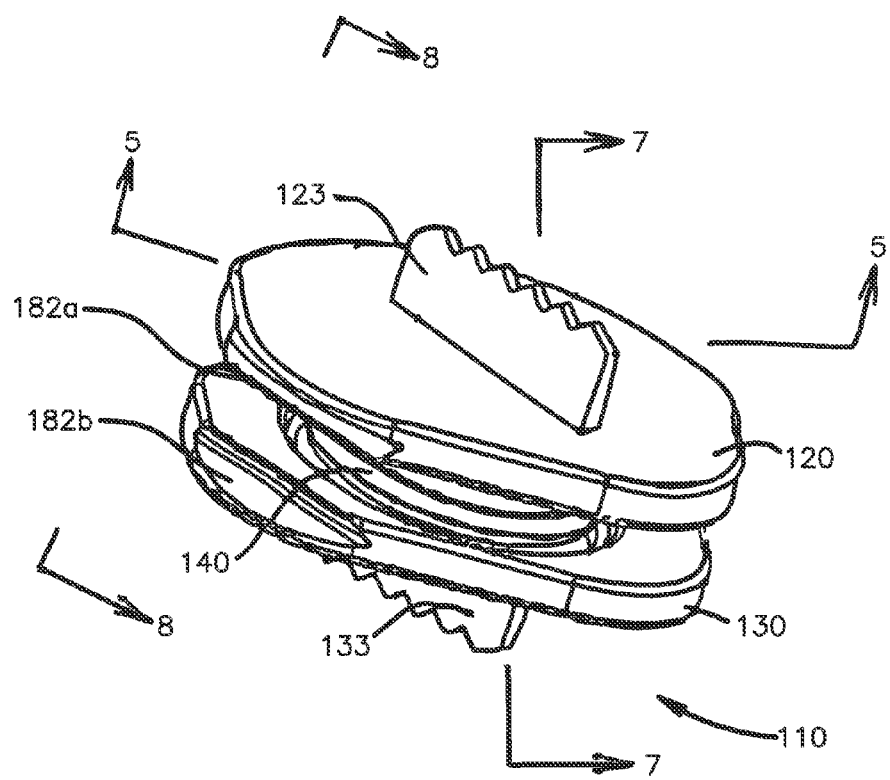
FIG. 4 is a perspective view of another embodiment of an implant device in accordance with the present invention.

Referring specifically to FIGS. 1-3, an intervertebral implant device 10 includes an upper part in the form of upper plate 20, a lower part in the form of lower plate 30 and a core element 40. The upper plate 20 includes an upper surface 21 and a lower convex surface 22. An anchor 23 with teeth 24 is designed to fit tightly and securely into a slot formed in an upper vertebrae with the upper surface 21 adjacent the lower surface of the upper vertebrae. Similarly, the lower plate 30 includes a lower surface 31, an upper convex surface 32 and an anchor 33 with anchor teeth 34. When the device 10 is implanted, the anchor 33 fits tightly in a slot formed in a lower vertebrae with the lower surface 31 adjacent the upper surface of the lower vertebrae.

The anchors 23, 33 are parallel to a major longitudinal plane through the implant device 10. The parallel orientation of the anchors 23, 33 relative to the major longitudinal plane of the implant device is advantageous for insertion of the device into the intervertebral space.

The core 40 includes an upper concave portion 41, a lower concave portion 42 and a circumferential groove 43. The upper concave portion 41 and lower concave portion 42 abut lower convex surface 22 of upper plate 20 and upper convex surface 32 of lower plate 30, respectively. As a result, the convex surfaces 22, 32 each provide an articulating surface with the upper concave portion 41 and lower concave portion 42 of the core 40, respectively. Circumferential groove 43 is designed to engage with an insertion tool for use during insertion of the implant device 10 in order to properly manipulate the core 40 between upper plate 20 and lower plate 30.

The upper plate 20 and lower plate 30 may be formed of an appropriate metallic material such as CoCr or titanium. Similarly, the core element 40 may be composed of the same or different appropriate metallic material as the upper plate 20 and lower plate 30.

The implant device 10 can be inserted as a single piece assembly or as individual components, namely upper plate 20, lower plate 30 and core element 40. Advantageously, implant device 10 can be inserted through either a lateral or anterolateral approach, thus preserving the anterior and posterior longitudinal ligaments. Alternatively, implant device 10 can be inserted through an anterior approach. The implant device 10 replicates the moving nucleus within an intervertebral disc. The stability of the upper plate, lower plate and core element is provided in part due to the preservation of all of the anterior and posterior longitudinal ligaments resulting from a lateral or anterolateral approach.

Insertion of the implant device 10 may be provided by a suitable surgical technique. For example, in a lumbar spine surgical technique of one advantageous method, one can generally use either a lateral or anterolateral approach to gain access to the pathologic level of the lumbar spine. However other techniques including an anterior approach can be used. Of course in the embodiment of FIGS. 1-3, since the anchors 23, 33 are in transverse planes, this embodiment, as shown, would more preferably be inserted only laterally.

During lateral or anterolateral insertion, upper and lower slots are formed in respective upper and lower vertebrae for accommodating anchors 23, 33. Lateral discectomy preserves all anterior and posterior longitudinal ligaments and some of the original disc annulus in order to allow for adequate upper plate and lower plate coverage to prevent subsidence, i.e., the unintentional movement of the upper plate relative to the lower plate. The implant device 10 is pre-assembled by inserting core 40 between upper plate 20 and lower plate 30 and the entire implant device 10 is inserted into the intervertebral space for attachment to the upper and lower vertebrae.

Referring generally to FIGS. 4-15, implant device 110 is another embodiment of the present invention. Similar elements to those of device 10 are similarly numbered but increased by 100 in FIGS. 4-15. FIGS. 4-7 and 9 depict the implant device in a neutral position and FIGS. 10-15 depict the implant device 10 in various different operative orientation positions.

Referring now specifically to FIGS. 4-15, implant device 110 comprises upper plate 120, lower plate 130 and core 140. Upper plate 120 includes an upper surface 121 and an anchor 123 with teeth 124. Lower plate 130 includes lower surface 131 and anchor 133 with teeth 134. When implanted, anchors 123, 133 fit tightly into slots formed in upper and lower vertebrae, respectively, with upper surface 121 and lower surface 131 being adjacent upper and lower vertebrae surfaces, respectively.

The anchors 123, 133 are shown at a 45 degree angle relate to the major longitudinal plane through the implant device 110. The 45 degree angle orientation of the anchors 123, 133 is advantageous for an anterolateral approach insertion. However, the anchors 123, 133 can be at any angle between 0 and 90 degrees relative to the major longitudinal plane.

Upper plate 120 and lower plate 130 are composed of a suitable metallic material which includes, but is not limited to, CoCr and titanium or a suitable ceramic material. Advantageously, upper plate 120 and lower plate 130 are composed of the same material although the plates may be composed of different materials.

Upper convex inlay 125 is disposed in recess 127 formed in a bottom surface of upper plate 120, and has a lower convex surface 126 opposite the recess 127. Similarly, lower convex inlay 135 is disposed in recess 137 of lower plate 130 with an upper convex surface 136 opposite the recess 137. Upper convex inlay 125 and lower convex inlay 135 may be composed of an appropriate material including various plastics and polymers such as polyethylene, as well as a ceramic material.

Formed in the bottom surface of the upper plate 120, surrounding recess 127, is an upper groove 128. Upper groove 128 extends 360 degrees around the lower convex surface 126. A lower groove 138 is similarly formed in an upper surface of lower plate 130 surrounding recess 137, and extending 360 degrees around the upper convex surface 136.

Within the upper groove 128 are groove wall surfaces 129 including groove floor surfaces 129*a*, 129*c*, 129*e*, 129*g* and groove side wall surfaces 129*b*, 129*d*, 129*f*, 129*h*. Depicted in FIGS. 4-15, groove floor surfaces 129*a*, 129*c*, 129*e*, 129*g* are parallel to a horizontal plane. Alternatively, groove floor surfaces 129*a*, 129*c*, 129*e*, 129*g* can be at an angle relative to a horizontal plane. For example, in one alternative embodiment, the groove floor surfaces 129*a*, 129*c*, 129*e*, 129*g* can slope upward as they extend radially.

Within lower groove 138 are groove wall surfaces 139 including groove floor surfaces 139*a*, 139*c*, 139*e*, 139*g* and groove side wall surfaces 139*b*, 139*d*, 139*f*, 139*h*. Like groove floor surfaces 129*a*, 129*c*, 129*e*, 129*g*, groove floor surfaces 139*a*, 139*c*, 139*e*, 139*g* are parallel to a horizontal plane. Alternatively, groove floor surfaces 139*a*, 1139*c*, 139*e*, 139*g* can slope downwardly, as they extend radially. For example, in one alternative embodiment, groove surfaces 139*a*, 139*c*, 139*e*, 139*g* can slope downwardly at a 5 degree angle.

Core 140 has upper concave portion, i.e., concave surface 141, and lower concave portion, i.e., concave surface 142, and circumferential external groove 143. Upper concave surface 141 provides an articulating surface with lower convex surface 126 and lower concave surface 142 provides an articulating surface with upper convex surface 136.

Figure 5:
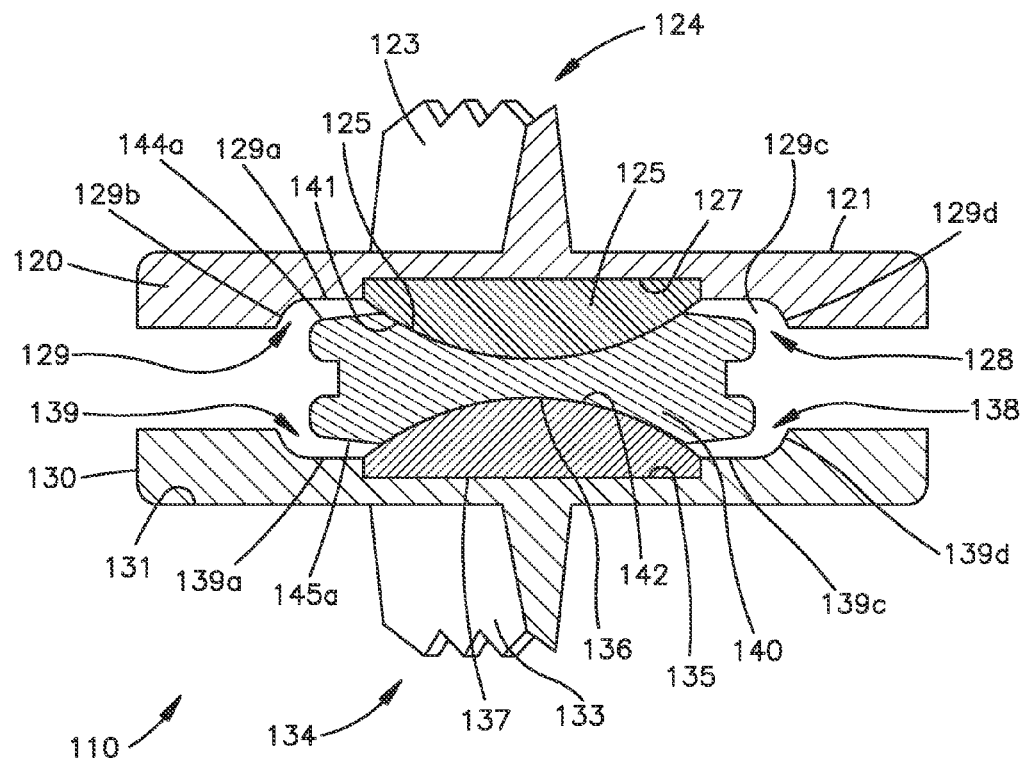
FIG. 5 is a cross sectional view of the implant device of FIG. 4 taken in the plane of line 5-5 of FIG. 4.
Figure 6:
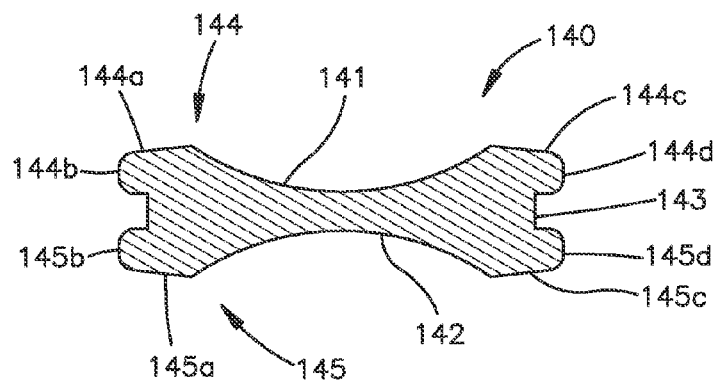
FIG. 6 is a core element of the implant device of FIG. 5.
Figure 7:
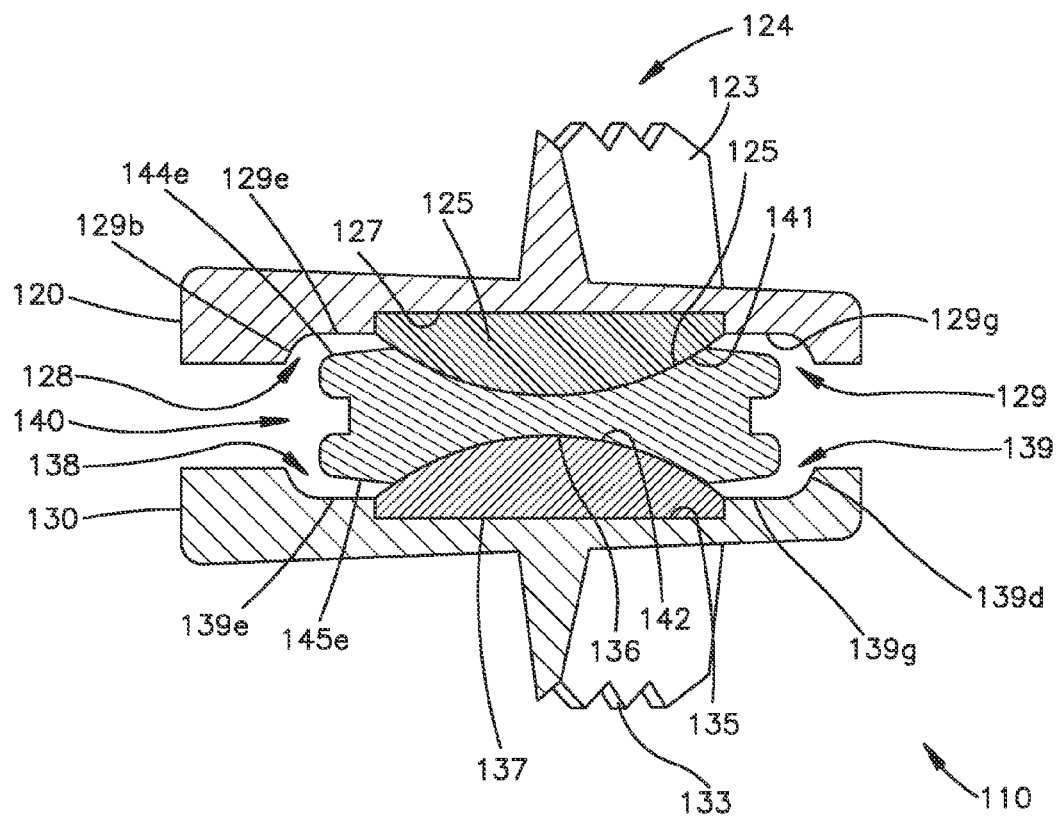
FIG. 7 is a cross sectional view of the device of FIG. 4 taken in the plane of line 7-7 of FIG. 4.
Figure 9:
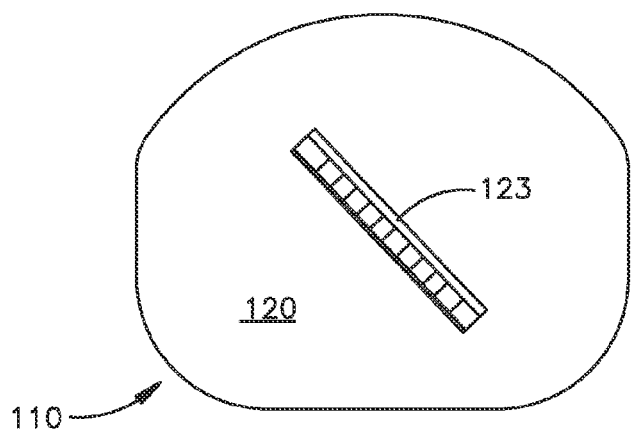
FIG. 9 is a top plan view of the implant device of FIG. 4.

Referring now specifically to FIG. 6 along with FIGS. 5 and 7, core element 140 includes upper surfaces 144 and lower surfaces 145. The upper surfaces 144 include upper angled surfaces 144*a*, 144*c*, 144*e*, 144*g* and upper circumferential surfaces 144*b*, 144*d*, 144*f*, 144*h*. The lower surfaces 145 include angled surfaces 145*a*, 145*c*, 145*e*, 145*g* and lower circumferential surfaces 145*b*, 145*d*, 145*f*, 145*h*.

In the alternative embodiment in which the upper groove floor surfaces 129*a*, 129*c*, 129*e*, 129*g* and lower groove floor surfaces 139*a*, 139*c*, 139*e*, 139*g* are sloped, upper angled surfaces 144*a*, 144*c*, 144*e*, 144*g* would be sloped at an angle in an opposite direction to that of upper groove floor surfaces 129*a*, 129*c*, 129*e*, 129*g* and lower angled surfaces 145*a*, 145*c*, 145*e*, 145*g* would be sloped at an angle in the opposite direction to that of lower groove floor surfaces 139*a*, 139*c*, 139*e*, 139*g*.

The upper and lower core angled surfaces 144*a*, 144*c*, 144*e*, 144*g* and 145*a*, 145*c*, 145*e*, 145*g*, sloping away from the upper and lower groove floor surfaces 129*a*, 129*c*, 129*e*, 129*g* and 139*a*, 139*c*, 139*e*, 139*g*, results in a larger gap being formed between upper angled surfaces 144*a*, 144*c*, 144*e*, 144*g* and upper groove floor surfaces 129*a*, 129*c*, 129*e*, 129*g*, and between lower angled surfaces 145*a*, 145*c*, 145*e*, 145*g* and lower groove floor surfaces 139*a*, 139*c*, 139*e*, 139*g* when implant device 110 is in its neutral position, as compared with a gap that would be formed were the respective core surfaces not angled. The comparatively larger gap provides enhanced relative movement of the upper part 120 relative to the lower part 130. In the alternative embodiment where the groove floor surfaces 129, 139 are sloped in a direction opposite to that of the respective core angled surfaces, an even larger gap would be formed, thus providing additional relative movement between the upper plate 120 and lower plate 130.

Device 110 is inserted between adjacent vertebrae in a manner similar to that described above with regard to implant 10 except that with the anchors oriented at 45 degrees this implant would be inserted anterolaterally in one advantageous method. Accordingly, implant 110 is inserted into the intervertebral space as a single unified device with core 140 disposed between upper plate 120 and lower plate 130 or as individual components. Device 110 provides limited universal movement of the upper plate 120 with respect to the lower plate 130 as well as lateral translational movement of the upper plate 120 relative to the lower plate 130. Limitation of the universal movement and horizontal translation is provided by the interaction of the core 140 with the upper groove 128 and lower groove 138 as described in detail with regard to FIGS. 10-15.

Figure 10:
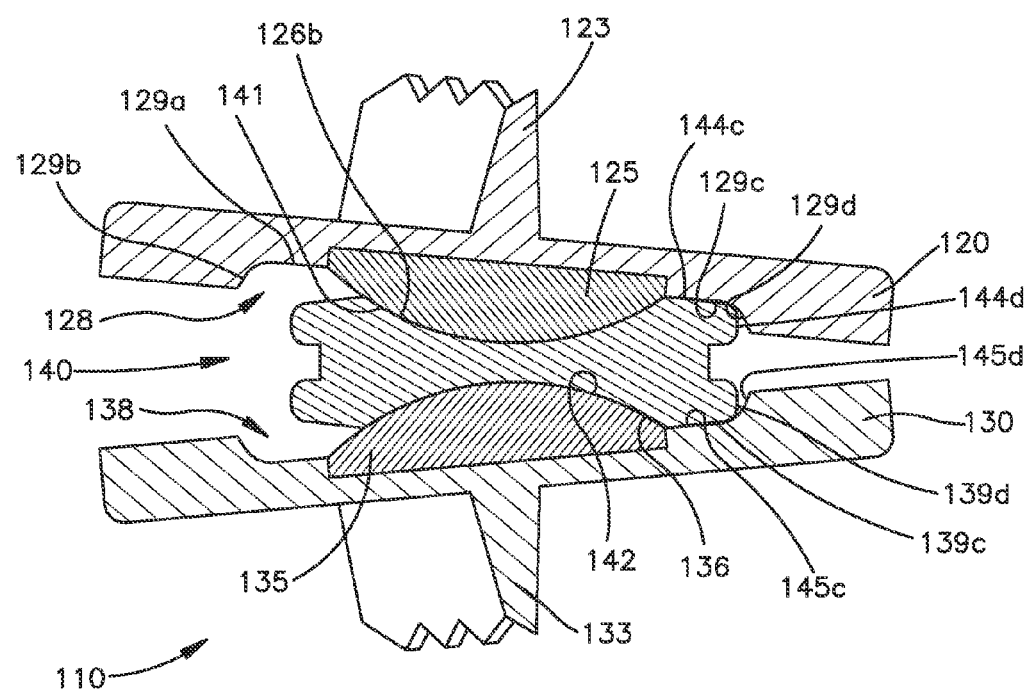
FIG. 10 is a cross sectional view of the implant device of FIG. 4 taken in the plane of line 5-5 of FIG. 4 depicting a lateral right bend position.
Figure 11:
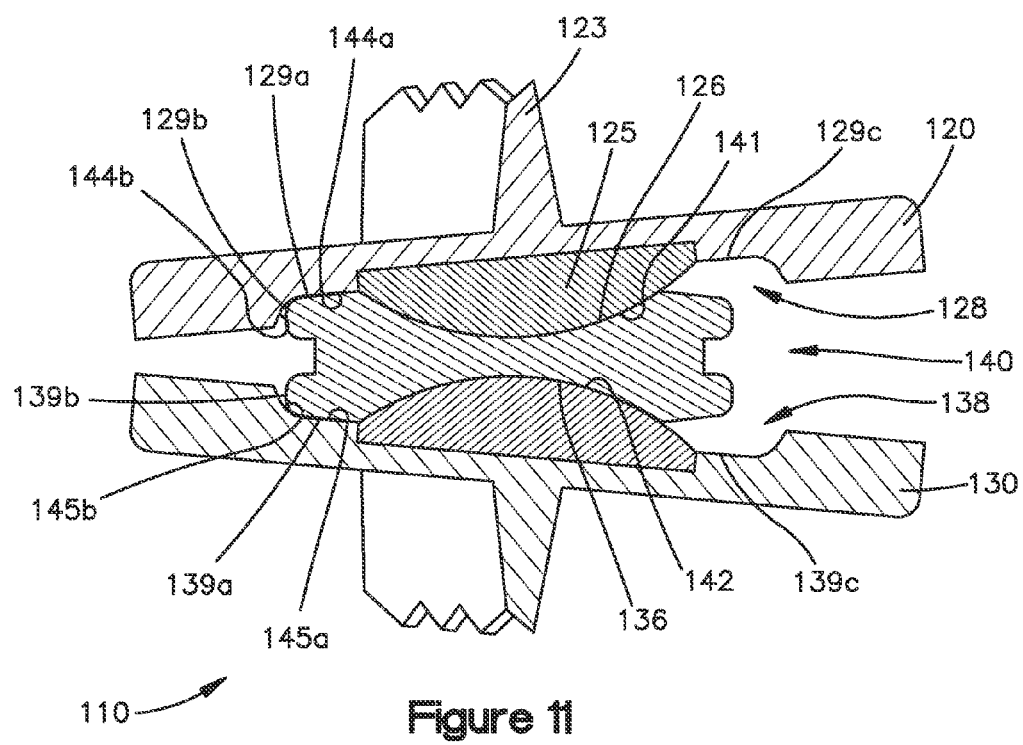
FIG. 11 is a cross sectional view of the implant device of FIG. 4 taken in the plane of line 5-5 of FIG. 4 depicting a left lateral bend position.

Referring now specifically to FIGS. 10 and 11, implant device 110 provides for right lateral bending (FIG. 10) and left lateral bending (FIG. 11). During a right lateral bend, convex surface 126 of the upper part and upper convex surface 136 of the lower part articulate along respective upper concave surface 141 and lower concave surface 142, respectively, of core 140. As a result, during a right lateral bend, core 140 slides into grooves 128, 138, with upper angled surface 144*c* abutting upper groove floor surface 129*c*, upper circumferential surface 144*d* abutting upper groove side wall surface 129*d*, lower angled surface 145*c* abutting lower groove floor surface 139*c*, and lower circumferential surface 145*d* abutting lower groove side wall surface 139*d*, in a maximum right lateral bend as depicted in FIG. 10. Similarly, during a left lateral bend, the upper plate 120 and lower plate 130 pivot towards one another along the convex surfaces 126, 136 which articulate with concave surfaces 141, 142, respectively, of core 140 so that upon a maximum left lateral bend, upper core surfaces 144*a*, 144*b* and lower core surface 145*a*, 145*b* will be disposed in grooves 128, 138 of upper plate 120, lower plate 130, respectively, and abut corresponding wall surfaces of the respective groove 128, 138

Limitation on the mobility of the upper plate 120 relative to the lower plate 130 is provided by upper core surfaces 144 and lower core surfaces 145 abutting corresponding groove surfaces 129, 139. For example, during a right lateral bend, at its maximum point, upper core surface 144c abuts upper groove floor surface 129c, upper circumferential surface 144d abuts upper groove side wall surface 129d, lower core surface 145c abuts lower groove floor surface 139c and lower circumferential surface 145d abuts lower groove side wall surface 139d. Similarly, during a left lateral bend, at its maximum point, upper core surfaces 144a, 144b abut upper groove surfaces 129a, 129b, respectively, and lower core surfaces 145a, 145b abut lower groove surfaces 139a, 139b, respectively.

Figure 12:
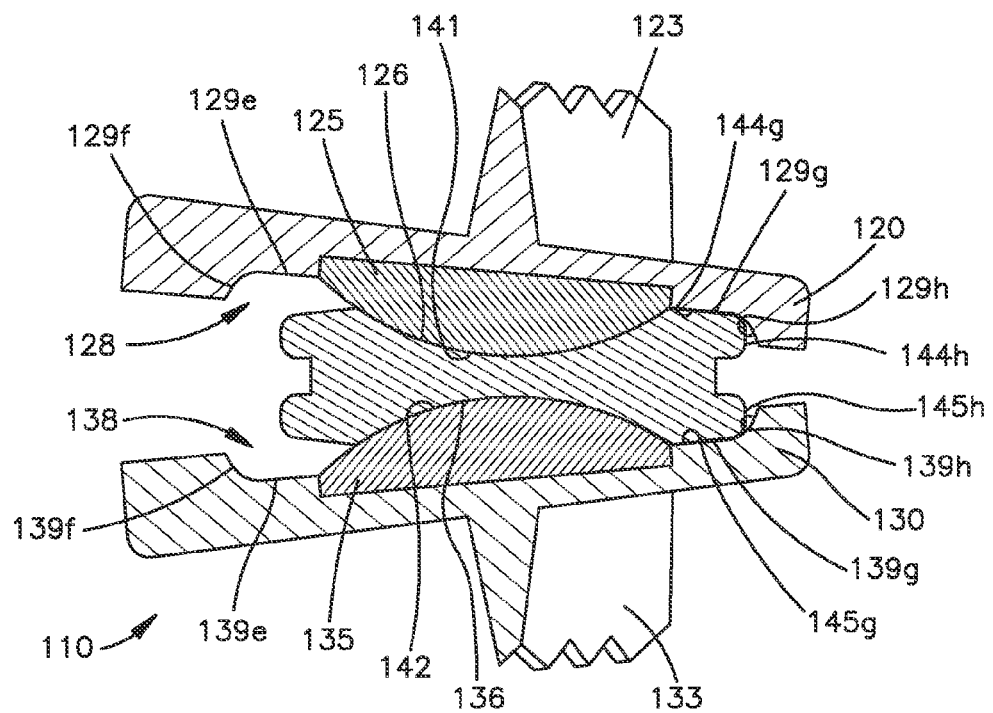
FIG. 12 is a cross sectional view of the implant device of FIG. 4 taken in the plane of line 7-7 of FIG. 4 shown in an extension position.

Referring now to FIG. 12, in an extension position, lower convex surface 126 and upper convex surface 136 will articulate along upper concave surface 141 and lower concave surface 142 of core 140, respectively. In a maximum extension position depicted in FIG. 12, upper core surfaces 144g, 144h and lower core surfaces 145g, 145h are disposed in grooves 128, 138 and abut corresponding groove surfaces, namely upper core surfaces 144g, 144h abut groove surfaces 129g, 129h, respectively, and lower core surfaces 145g, 145h abut groove surfaces 139g, 139h, respectively.

Figure 13:
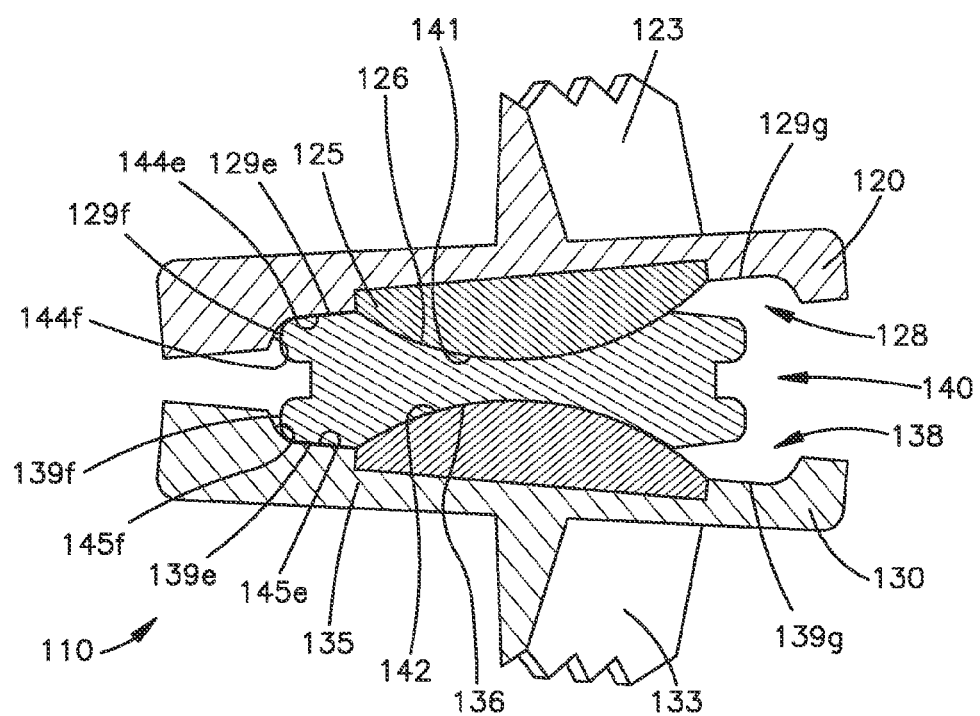
FIG. 13 is a cross sectional view of the implant device of FIG. 4 taken in the plane of line 7-7 of FIG. 4 depicted in a flexion position.

Referring now to FIG. 13, in a flexion position of device 110, at its maximum flexion position, upper core surfaces 144e, 144f and lower core surface 145e, 145f will be disposed in upper groove 128 and lower groove 138, respectively, and abut corresponding groove wall surfaces.

As with the limitation of right and left lateral bending, maximum flexion and extension is provided by upper core surfaces 144 and lower core surfaces 145 interacting and abutting upper and lower groove wall surfaces 129, 139, respectively.

Figure 14:
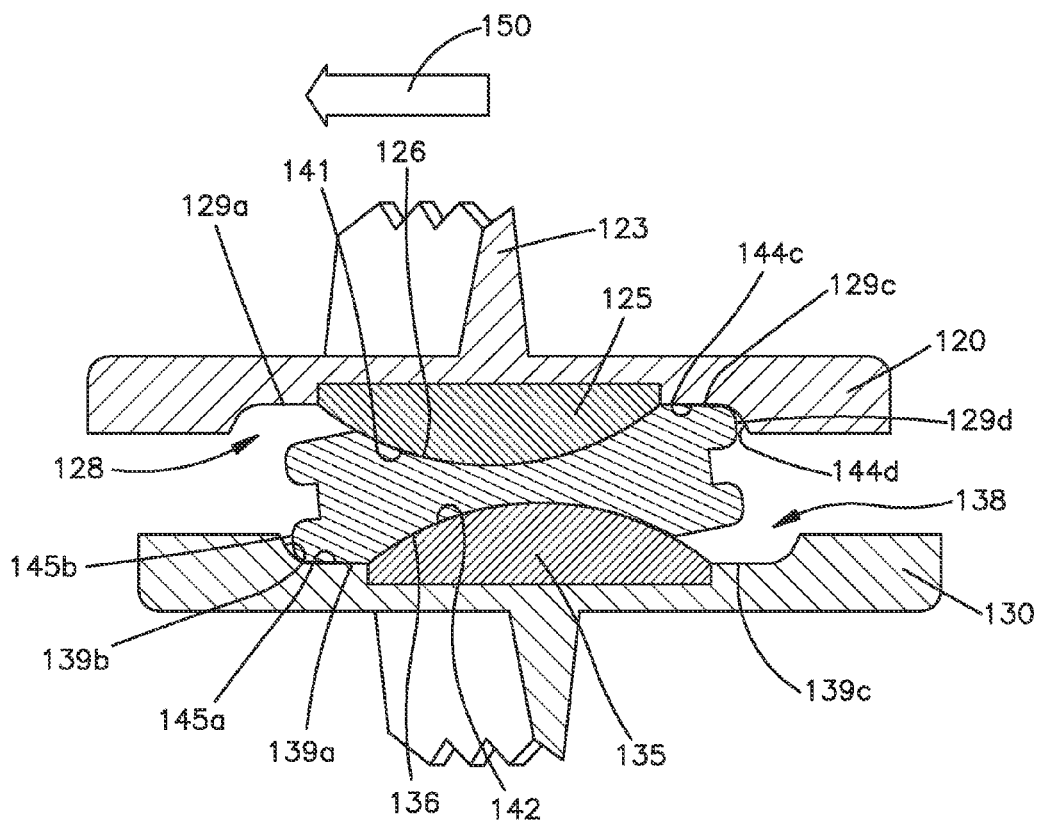
FIG. 14 is the implant device of FIG. 4 taken in the plane of line 5-5 of FIG. 4 depicted in a lateral translation position.
Figure 15:
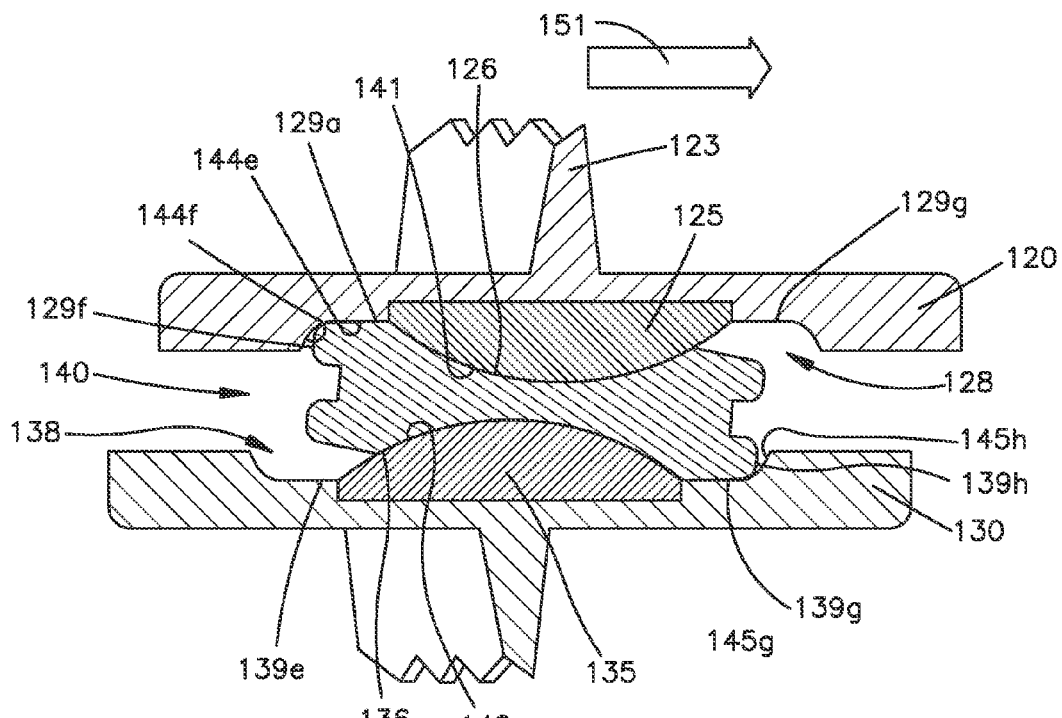
FIG. 15 is a cross sectional view of the implant device of FIG. 4 taken in the plane of line 7-7 of FIG. 4 shown in a rear translation position.
Figure 16:
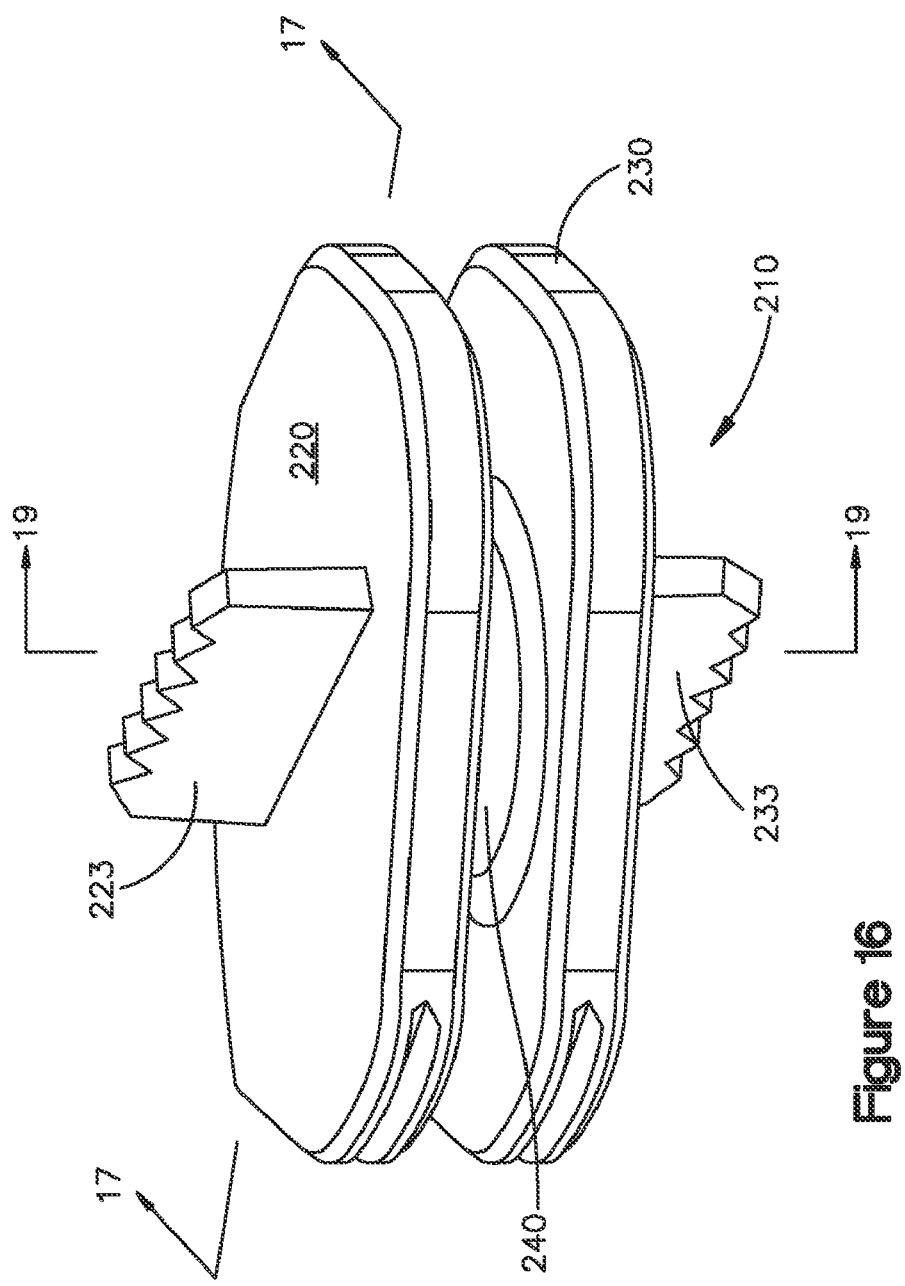
FIG. 16 is a perspective view of another embodiment of an implant device in accordance with the present invention.
Figure 17:
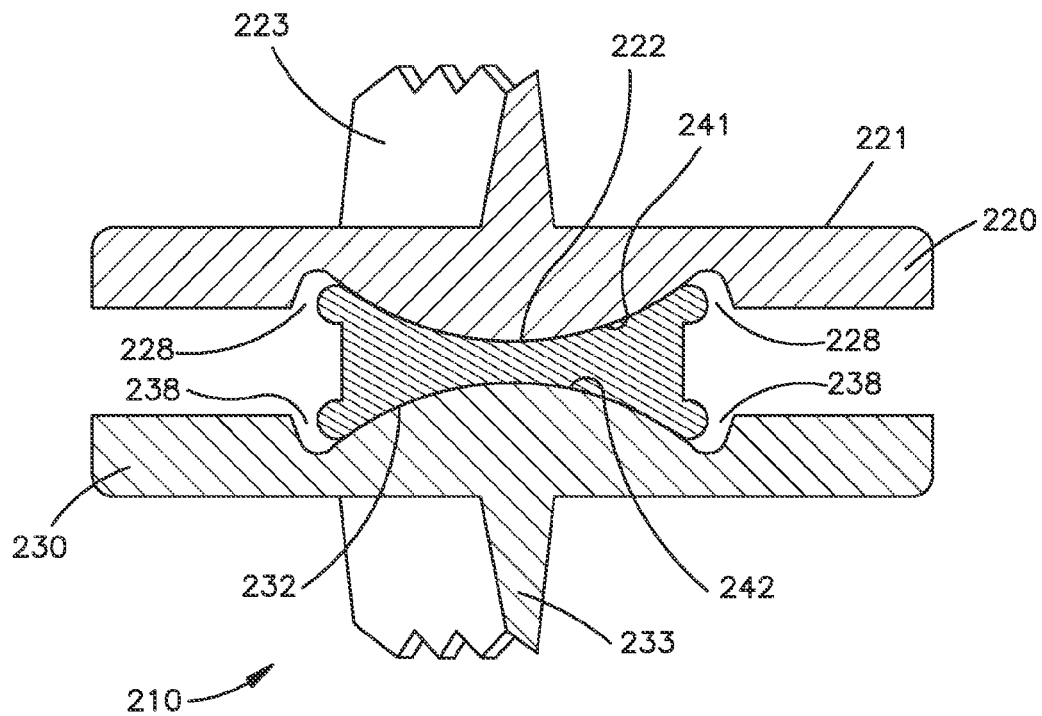
FIG. 17 is a cross sectional view of the implant device of FIG. 16 taken in the plane of line 17-17 of FIG. 16.
Figure 18:
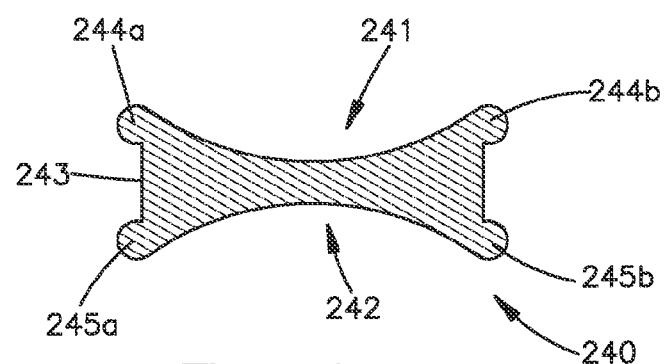
FIG. 18 is a core element of the device of FIG. 17.
Figure 19:
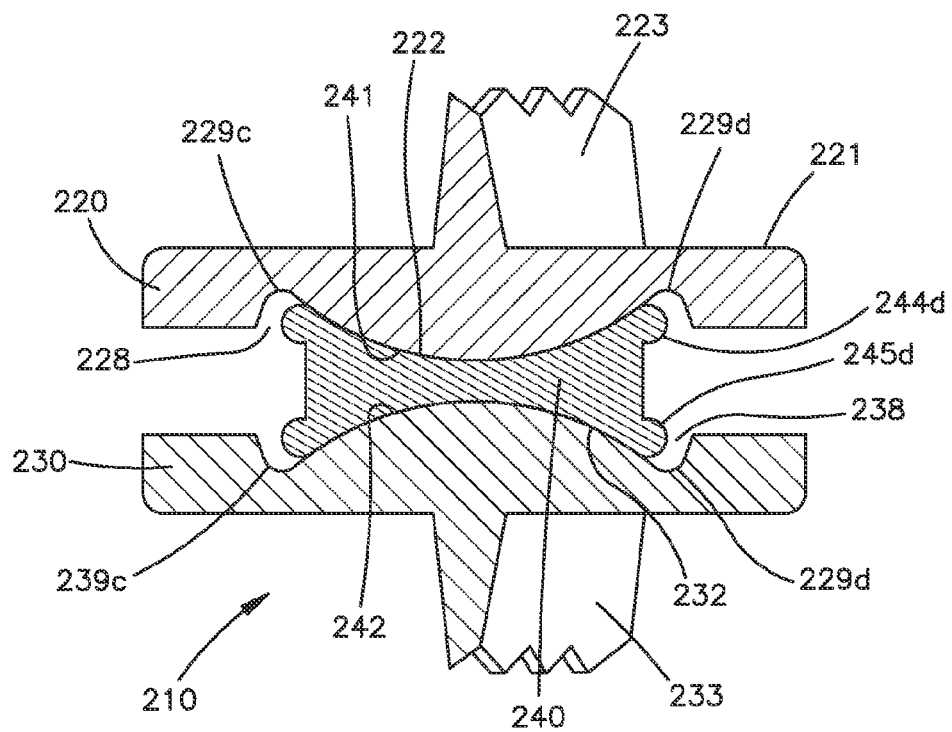
FIG. 19 is a cross sectional view of the implant device of FIG. 16 taken in the plane of line 19-19 of FIG. 16.
Figure 20:
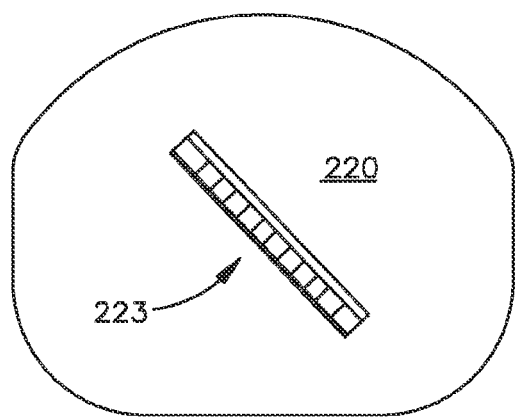
FIG. 20 is a top plan view of the device of FIG. 16.

Implant device 110 also provides lateral translation in all 360 degrees. FIG. 14 depicts a lateral translation of the implant device 110 wherein the upper part moves in the direction of arrow 150 relative to the lower part and FIG. 15 depicts a rear translation of implant device 110 wherein the upper part moves in a rear direction relative to the lower part as indicated by arrow 151. Translation of upper plate 120 relative to lower plate 130 in a translational direction, e.g., direction 150 or 151, is provided by the sliding articulation of the lower convex surface 126 of upper plate 120 with the upper concave surface 141 of core 140 in an opposite direction relative to the articulation of the upper convex surface 136 of lower plate 130 along lower concave surface 142 of core 140.

Referring specifically to the lateral translation in FIG. 14, a translation of upper plate 120 in the direction of arrow 150, relative to lower plate 130, results in lower core surfaces 145a, 145b being slid into groove 138 and upper core surfaces 144c, 144d sliding into upper groove 128, with lower core surface 145a abutting lower groove floor surface 139a, lower circumferential surface 145b abutting lower groove side wall surface 139b, upper core surface 144c abutting upper groove floor surface 129c, and upper circumferential core surface 144d abutting upper side wall surface 129d, in its maximum translation position of implant device 110. In the rear translation depicted in FIG. 15, lower core surfaces 145g, 145h slide into groove 138 and abut groove surfaces 139g, 139h, respectively, and upper core surfaces 144e, 144f slide into groove 128 and abut groove surfaces 129e, 129f, respectively, when implant 110 is in a maximum rear translation position.

Referring now to FIGS. 8a and 8b, upper plate 120 includes a pair of grooves 182a, 182b and lower plate 130 includes a pair of grooves 184a, 184b. The pairs of grooves 182a, 182b; 184a, 184b are dimensioned to accommodate the use of insertion tool 190 having upper protrusions 192a, 192b and lower protrusions 194a, 194b which engage upper grooves 182a, 182b and lower grooves 184a, 184b, respectively. The insertion tool 190 and in particular central raised portions 195a and 195b, with central ribs 196a and 196b maintain the implant device in a unified form during manipulation and insertion.

Referring generally now to FIGS. 16-26, implant device 210 represents another form of an implant device in accordance with the present invention. Similar elements to those of devices 10, 110 are similarly numbered by increase by 100 or 200, respectively.

Implant 210 includes an upper plate 220, a lower plate 230 and a core element 240. As with device 110, anchors 223, 233 are at a 45 degree angle relative to a major longitudinal plane through a midpoint of the implant device 210. Thus, the relative angle of the anchors 223, 233 provide for an anterolateral approach for the insertion and implantation of the implant device 210.

Unlike device 110, lower convex surface 222 and upper convex surface 232 are formed in the lower and upper surfaces of the upper and lower plates 220, 230, respectively, rather than being convex surfaces of separate inlay elements.

FIGS. 16-20 depict the implant 210 in its neutral position whereby there is a circumferential grooves 228, 238 formed around lower convex surface 222 and upper convex surface 232, respectively.

FIGS. 21 and 22 depict left and right lateral bends, respectively, which are provided by implant 210 as a result of lower convex surface 222 articulating with upper concave surface 241 and upper convex portion 232 articulating with upper concave surface 242. For example, during a left lateral bend (FIG. 21), upper core surface 244a and lower core surface 245a slide into grooves 228, 238, respectively. In a maximum left lateral bend, core surfaces 244a, 245a abut groove surfaces 229a, 239a, respectively.

Similarly, during a right lateral bend (FIG. 22), the upper plate 220 and lower plate 230 articulate along convex surfaces 222, 232. In a maximum right lateral bend, upper core surface 244b abuts upper groove surface 229b and lower core surface 245b abuts lower groove surface 239b, thus limiting lateral movement of upper plate 220 relative to lower plate 230. As with the implant device 110, limitation of movement is provided by the core surfaces 144, 145 abutting groove surfaces 129, 139, respectively.

Figure 23:
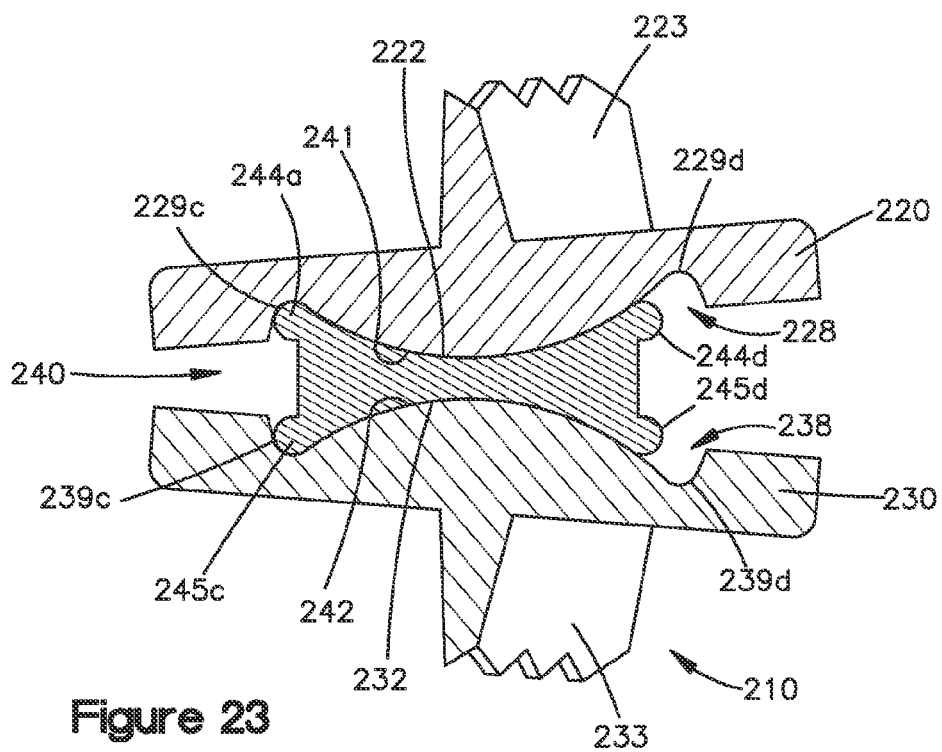
FIG. 23 is a cross sectional view of the implant device of FIG. 16 taken in the plane of line 19-19 of FIG. 16, shown in an flexion position.
Figure 24:
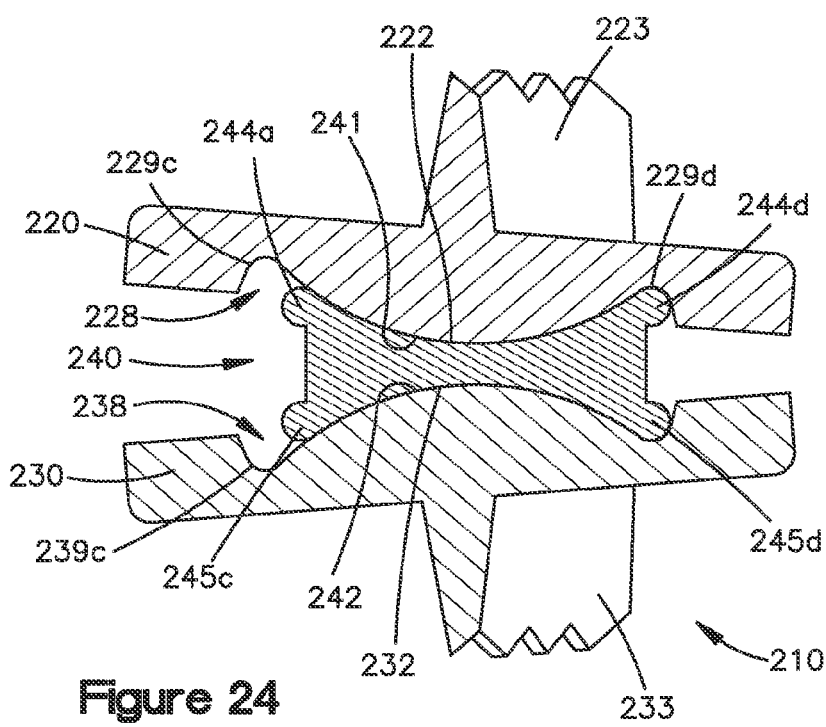
FIG. 24 is a cross sectional view of the implant device of FIG. 16 taken in the plane of line 19-19 of FIG. 16, shown in a extension position.

Referring now to FIGS. 23 and 24, implant 210 provides for flexion and extension by having the articulating surfaces of the upper plate 220 and lower plate 230 slide along the abutting upper concave surface 241 and lower concave surface 242, respectively, as depicted in FIGS. 23 and 24, respectively.

Figure 25:
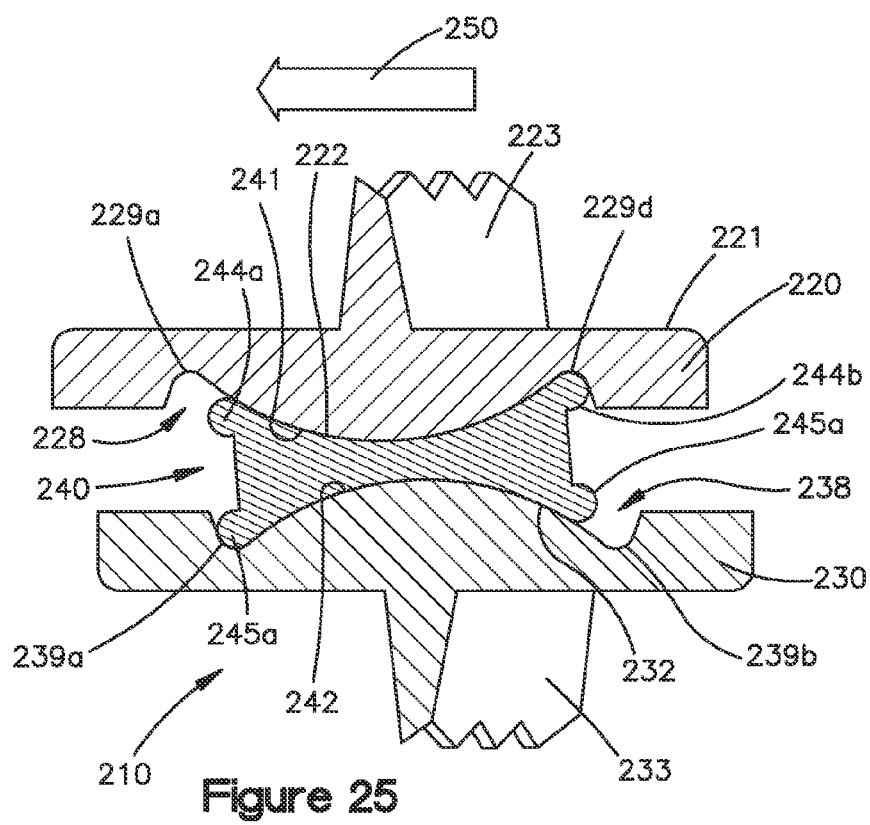
FIG. 25 is a cross sectional view of the implant device of FIG. 16 taken in the plane of line 17-17 of FIG. 16, shown in a left lateral translation position.
Figure 26:
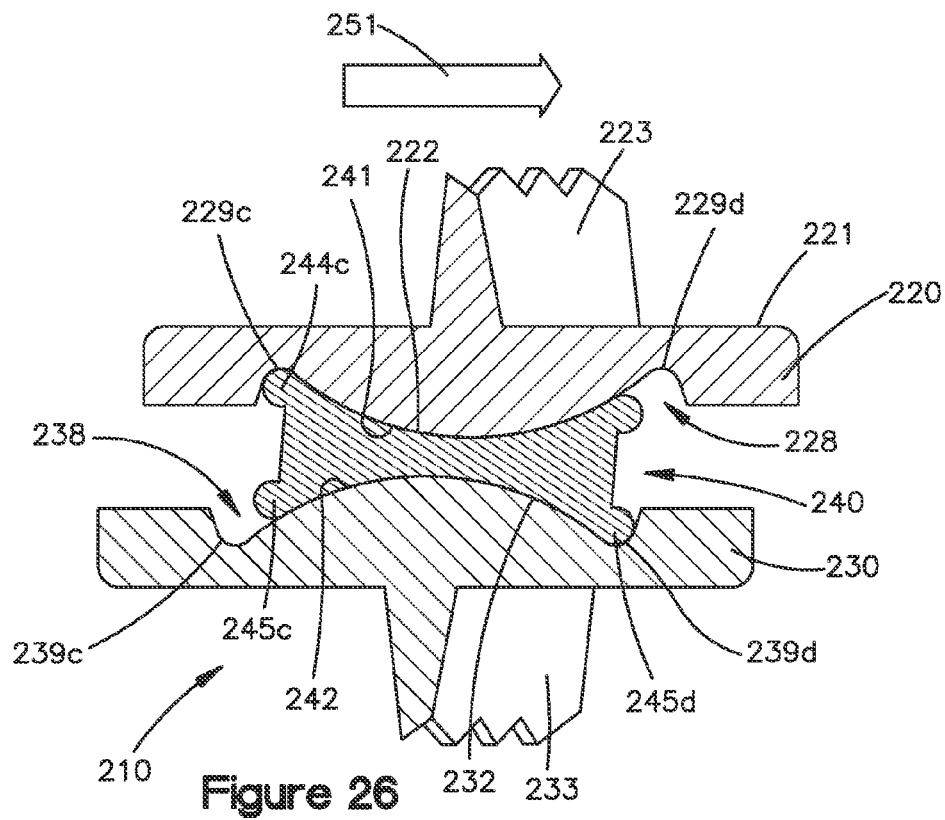
FIG. 26 is a cross sectional view of the implant device of FIG. 16 taken in the plane of line 19-19 of FIG. 16, shown in a rear lateral translation position.

Referring now to FIGS. 25 and 26, left lateral translation and rear translation of the upper plate 220 with respect to the lower plate 230 are depicted, respectively. Translation of the upper plate 220 relative to the lower plate 230 is provided by the upper plate 220 moving in a lateral direction opposite that of the lower plate 230. For example, during left lateral translation depicted in FIG. 25, the upper plate 220 of implant 210 is translated in the direction of arrow 250 relative to the lower plate 230, resulting in upper core surface 244b and lower core surface 245a being disposed in upper groove 228 and lower groove 238, respectively. During the rear translation of the upper plate 220 of implant 210 in the direction of arrow 251 relative to the lower plate 230, upper core surface 244c and lower core surface 245d will be disposed in upper groove 228 and lower groove 238, respectively.

FIGS. 27-31 show another embodiment 310 of an implant device in accordance with the present invention. Implant 310 differs from implants 110 and 210 by having upper and lower anchors 323, 333 which are parallel to a transverse plane running through the major longitudinal axis of the implant device 310. Like implant 10, the parallel orientation of the anchors 323, 333 with respect to the major longitudinal axis provides for a lateral insertion approach.

Further, like implant devices 10 and 210, articulating convex surfaces 322, 332 are formed on the lower and upper surfaces of upper plate 320, lower plate 330, respectively.

Figure 27:
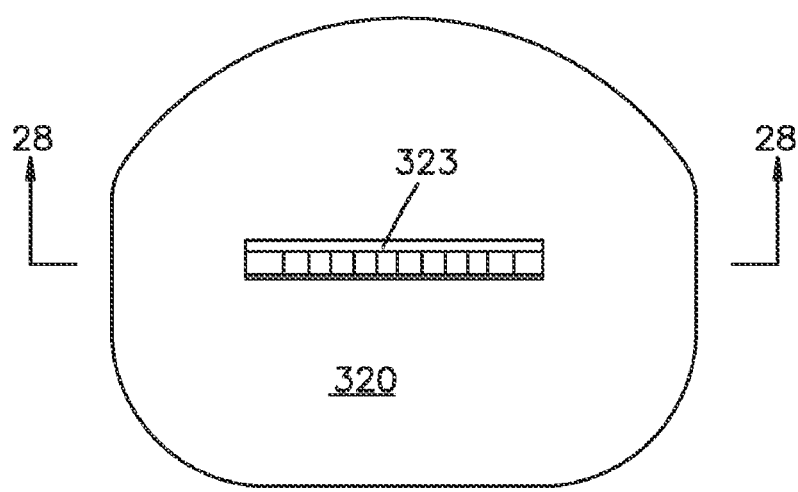
FIG. 27 is a top plan view of another embodiment of the implant device in accordance with the present invention.
Figure 28:
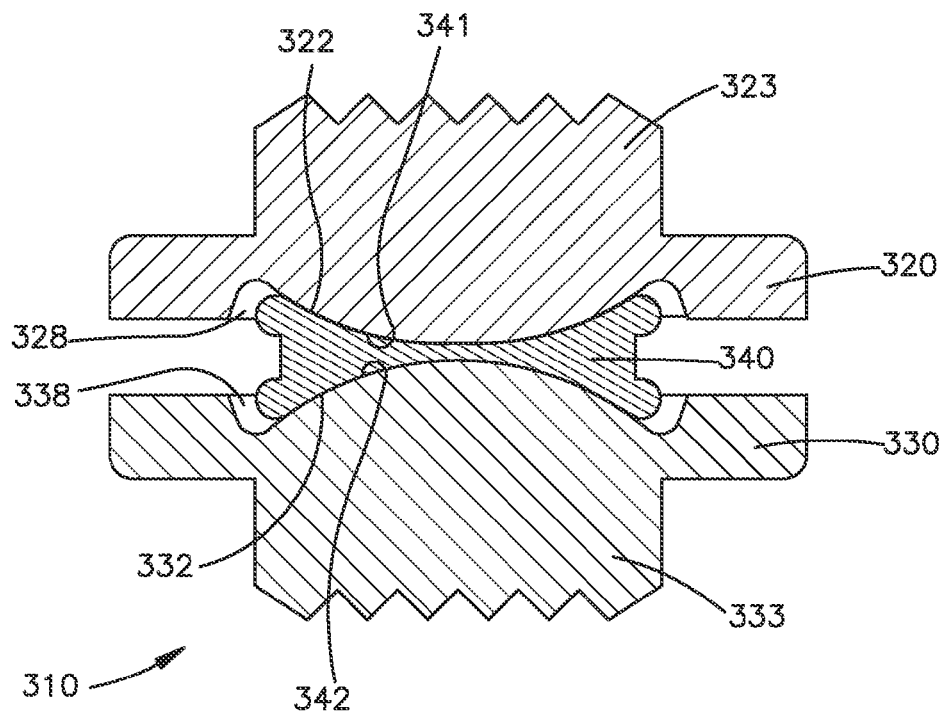
FIG. 28 is a cross sectional view of the implant device of FIG. 27 taken in the plane of line 28-28 of FIG. 27.
Figure 29:
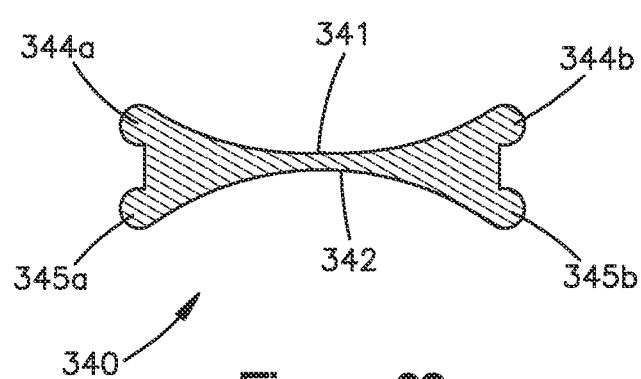
FIG. 29 is a core element of the implant device of FIG. 28.
Figure 30:
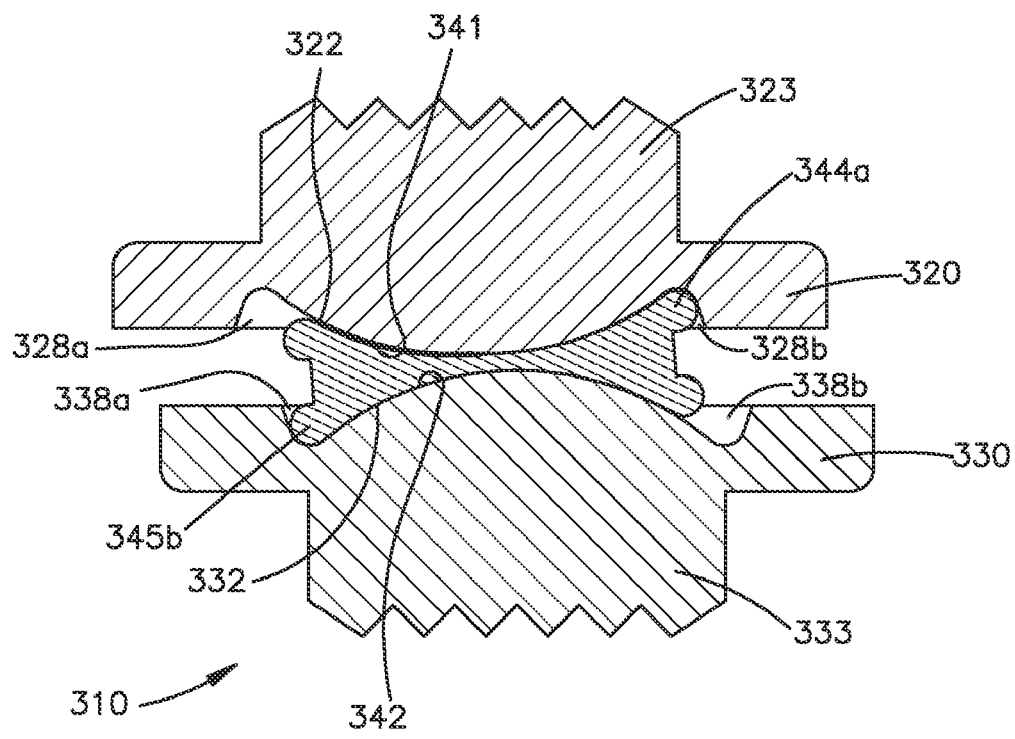
FIG. 30 shows the implant device of FIG. 27 taken in the plane of line 28-28 of FIG. 27, shown in a lateral translation position.
Figure 31:
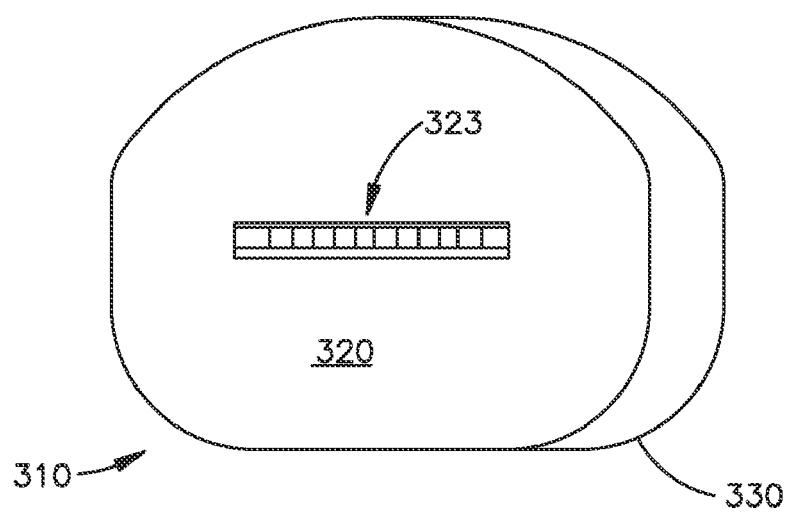
FIG. 31 is a top plan view of FIG. 30.

Like implants 110 and 210, implant device 310 allows for limited universal movement via extension, flexion, left and right lateral bending, and translation with the limitation of movement provided by the interaction of core 340 with grooves 328, 338. FIGS. 27-29 depict the implant in a neutral position and FIGS. 30 and 31 depict the implant 310 in a translation position. The aforementioned limited universal movement and translation occurs in a manner similar to that described above with regard to implant devices 110, 210.

Referring now specifically to FIG. 29, core 340 has a slightly broader concave surfaces 341, 342, i.e., a larger curvature radius, than the concave surfaces of cores 140, 240. As a result of the larger curvature radius of the concave surfaces 341, 342 of core 340, implant device 310 will have a larger degree of horizontal translation than implant devices 110, 210, while having the same degree of limited universal movement of lateral bending, flexion and extension as implant devices 110, 210.

The present implant devices provide features not present in other implant devices. For example, the present device provides enhanced relative movement between the upper part and lower part which includes translation of the upper part relative to the lower part. When implanted, the implant device of the present invention can provide natural movement of a patient's spinal column and movement between adjacent vertebrae where the implant device is inserted. The use of the present implant device with translation movement can be beneficial for implantation in patients with less severe degenerative disc disease and thus not require total disc replacement. In this instance, replacing only the nucleus pulposus of the intervertebral disc while leaving the disc annulus and the ligaments as intact as possible may benefit from the present implant device which provides limited translation movement. In one advantageous insertion technique, the intact ligaments provide the necessary support to accommodate the additional lateral and translational movement provided by the present implant device.

It will now be readily apparent to one of ordinary skill in the art that the present implant device provides advantages and features not shown in prior implants such as hydrogel/polymer nucleus replacement devices. For example, the present implant uses previously known materials which have been used in the field of arthroplasty. Further, the present implants allow for an initial secure and permanent fixation of the device using the anchors. Further, the present implants allow for the restoration of a normal nucleus movement which occurs during natural motion. In addition, the present implant allows for one to restore the natural disc height. Further, the present implant allows one to perform an adequate discectomy through a mini-open approach.

Although the invention has been described in considerable detail with respect to preferred embodiments thereof, it will be apparent that the invention is capable of numerous modifications and variations, apparent to those skilled in the art.

What is claimed is:

1. An intervertebral device for insertion between two adjacent vertebrae, comprising:
   an upper part having an upper surface for engaging an upper vertebrae and a lower surface having a convex portion;
   a lower part having a lower surface for engaging an adjacent, lower vertebrae and an upper surface having a convex portion; and
   a core element having an upper concave portion to operatively engage with said convex portion of said upper part and a lower concave portion to operatively engage with said convex portion of said lower part,
   wherein the upper and lower parts each have a groove located adjacent to and surrounding their respective convex portions, the groove having a groove floor surface adjacent the convex portion and a groove side wall surface located radially more distant from the convex portion than the groove floor surface and that extends from the groove floor surface toward the opposing part,
   wherein the core element comprises an upper surface surrounding the upper concave portion, the upper surface terminating in a circumferential surface, and further comprises a lower surface surrounding the lower concave portion, the lower surface terminating in a circumferential surface, and
   wherein the groove side wall surface of the upper and lower parts is constructed such that upon bringing the upper and lower parts together at an edge of the intervertebral device the terminal circumferential surface of the core element engages the groove side wall surface.

2. The intervertebral device of claim 1, including a circumferential groove in the core adapted for receiving an insertion instrument.

3. The intervertebral device of claim 1, wherein said upper part comprises an anchor for engaging a vertebrae.

4. The intervertebral device of claim 3, wherein said anchor is at a 45 degree angle relative to a transverse longitudinal plane through a major axis of said device.

5. The intervertebral device of claim 3, wherein said anchor is at an angle between 0 and 90 degrees relative to a transverse longitudinal plane through a major axis of said device.

6. The intervertebral device of claim 1, wherein said upper part has an upper inlay element dimensioned to be disposed in a recess formed therein; said upper inlay element having a lower surface that includes the convex portion of the upper part and
   said lower part has a lower inlay element dimensioned to be disposed in a recess formed therein; said lower inlay element having an upper surface that includes the convex surface portion of the lower part,
   wherein said upper part and said lower part are translatable relative to each other by sliding along said concave portions of said core element.

7. The intervertebral device of claim 6, wherein at least one of said upper part and said lower part comprises an anchor for engaging a vertebrae.

8. The intervertebral device of claim 6, wherein said anchor is at an angle between 0 and 90 degrees relative to a transverse longitudinal plane through a major axis of said implant.

9. The intervertebral device of claim 8, where said anchor is at a 45 degree angle relative to the transverse longitudinal plane.

10. The intervertebral device of claim 6, wherein said core element comprises a circumferential groove adapted for receiving an insertion instrument.

11. The device of claim 6, wherein each said inlay element is composed a material selected from the group consisting of metal, plastic and ceramic.

12. The device of claim 11, wherein said plastic comprises polyethylene.

13. The device of claim 6, wherein said upper groove has a groove floor surface at an angle relative to the horizontal; said lower groove has a groove floor surface at an angle relative to the horizontal; and said core element has upper angled surface and lower angled surface at respective angles in opposite directions to that of said upper groove floor surface and said lower groove floor surface, respectively.

14. The device of claim 13, wherein said upper groove floor surface and said lower groove floor surface mate with said upper angled surface and lower angled surface of said core during maximum movement of said upper part relative to said lower part.

15. The device of claim 6, wherein said upper groove has a groove floor surface parallel to the horizontal; said lower groove has a groove floor surface parallel to the horizontal; and said core element has upper angled surface and lower angled surface at respective angles sloping away from said upper groove floor surface and said lower groove floor surface, respectively.

16. The device of claim 15, wherein said upper groove floor surface and said lower groove floor surface mate with said upper angled surface and lower angled surface of said core during maximum movement of said upper part relative to said lower part.

17. The device of claim 6, wherein said upper part and said lower part remain parallel with respect to each other when said upper part and said lower part are laterally translated with respect to each other.

18. An intervertebral device for insertion between two adjacent vertebrae, comprising:
an upper part having an upper surface for engaging an upper vertebrae and a lower surface having a convex portion, the upper part having an upper groove located adjacent to and surrounding the convex portion, the upper groove having an upper groove floor surface located adjacent the convex portion and an upper groove side wall surface located radially more distant from the convex portion than the upper groove floor surface and extending vertically outward from the upper groove floor surface;
a lower part having a lower surface for engaging an adjacent lower vertebrae and an upper surface having a convex portion, the lower part having a lower groove located adjacent to and surrounding the convex portion, the lower groove having a lower groove floor surface located adjacent the convex portion and a lower groove side wall surface located radially more distant from the convex portion than the lower groove floor surface and extending vertically outward from the lower groove floor surface; and
a core element having an upper concave portion to operatively engage with said convex portion of said upper part and a lower concave portion to operatively engage with said convex portion of said lower part, the core element having upper and lower circumferential core surfaces surrounding and adjacent to the core concave portions, the upper and lower core surfaces terminating in a circumferential surface, whereby said upper part and said lower part are laterally translatable relative to each other by sliding along said concave portions of said core element, wherein the convex portion of the lower part is aligned with the convex portion of the upper part in one relative lateral position of the upper and lower parts, and at least a portion of said upper and lower core terminating circumferential surfaces abut at least a portion of the groove side wall surface of the upper and lower parts in a maximum bend position to the intervertebral device to limit movement of the upper and lower parts beyond the maximum bend position.

19. The device of claim 18, wherein each said convex portion of said upper part and lower part comprise a surface of a respective inlay element dimensioned to be disposed in a respective recess formed in each of said upper part and said lower part.

20. The device of claim 19, wherein said inlay element is composed a material selected from the group consisting of metal, plastic and ceramic.

21. The device of claim 20, wherein said plastic comprises polyethylene.

22. The device of claim 18, wherein:
said upper groove floor surface is at an angle relative to the horizontal;
said lower groove floor surface is at an angle relative to the horizontal; and
said upper and lower core surfaces are at angles in opposite directions to that of said upper groove floor surface and said lower groove floor surface, respectively.

23. The device of claim 22, wherein said upper groove floor surface and said lower groove floor surface mate with said upper angled surface and lower angled surface of said core, respectively, during a maximum bend position of said upper part relative to said lower part.

24. The device of claim 18, wherein said core element has an upper angled surface and a lower angled surface sloping away from groove floor surfaces of said upper groove and said lower groove, respectively.

25. The device of claim 24, wherein said upper groove floor surface and said lower groove floor surface mate with said upper angled surface and lower angled surface of said core, respectively, during a maximum bend position of said upper part relative to said lower part.

26. The intervertebral device of claim 18, wherein at least one of said upper part and said lower part comprises an anchor for engaging a vertebrae.

27. The intervertebral device of claim 26, wherein said anchor is at an angle between 0 and 90 degrees relative to a transverse longitudinal plane through a major axis of said device.

28. The intervertebral device of claim 27, wherein said anchor is at a 45 degree angle relative to the transverse longitudinal plane.

29. The intervertebral device of claim 18, wherein said core element comprises a circumferential groove adapted for receiving an insertion instrument.

30. The device of claim 18, wherein said upper part and said lower part remain parallel with respect to each other when said upper part and said lower part are laterally translated with respect to each other.

31. The intervertebral device of claim 18, wherein the convex portion of the lower part is vertically aligned with the convex portion of the upper part in said one relative lateral position of the upper and lower parts.

32. The intervertebral device of claim 18, wherein the groove side wall surface of the upper and lower parts is constructed such that upon bringing the upper and lower parts together at an edge of the intervertebral device the terminal circumferential surface of the core element engages the groove side wall surface.

* * * * *